United States Patent [19]

Warriner

[11] Plant 5,122

[45] Oct. 18, 1983

[54] ROSE PLANT 75-20031 JACDEW

[75] Inventor: William A. Warriner, Tustin, Calif.

[73] Assignee: Jackson & Perkins Company, Medford, Oreg.

[21] Appl. No.: 355,713

[22] Filed: Mar. 8, 1982

[51] Int. Cl.[3] ..... A01H 5/00

[52] U.S. Cl. ..... Plt./28

[58] Field of Search ..... Plt./28

*Primary Examiner*—Robert E. Bagwill

*Attorney, Agent, or Firm*—Klarquist, Sparkman, Campbell, Leigh, Whinston & Dellett

[57] ABSTRACT

A floribunda rose variety having a bush which blooms continuously through the growing season; glossy foliage; orange-red blooms which fade to lighter color before falling; little or no fragrance; numerous prickles.

1 Drawing Figure

This present invention relates to a new and distinct variety of rose plant of the floribunda class which was originated by me by crossing the variety America, U.S. Plant Pat. No. 3,682, with an unnamed variety.

The primary objective of this breeding was to produce a new rose variety of the floribunda class with abundant blooms and disease resistant foliage. This objective was substantially achieved along with other desirable improvements as evidenced by the following unique combination of characteristics which are outstanding in the new variety and which distinguish it from its parents, as well as from all other varieties of which I am aware:

1. A floribunda type bush, blooming continuously through the growing season.
2. Foliage glossy and nearly immune to rose powdery mildew.
3. Blooms of orange-red fading to a lighter color before falling.
4. Very little or no fragrance.
5. Numerous large and small prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—America, U.S. Plant Pat. No. 3,682.

*Pollen parent.*—Unnamed variety.

Classification:

*Botanical.*—Rosa hybrid.

*Commercial.*—Floribunda.

FLOWER

Observations made from specimens grown at Irvine, Calif. in November.

Blooming habit: Continuous.

Bud:

*Size.*—1" to 1⅛" when petals start to unfurl.

*Form.*—Blunt top.

*Color.*—When sepals first divide, Red 42A. When half blown, upper side of petals Red 43A; lower side of petals Red 42A.

*Sepals.*—Color: Outer surface Green 138A with a few stipitate glands. Three appendaged sepals lightly appendaged. Two unappendaged sepals hairy edged.

*Receptacle.*—Color: Green 138A. Shape: Funnel. Size: Large. Surface: Smooth.

*Peduncle.*—Length: Short. Surface: Prickly and glandular. Color: Bronzy. Strength: Stiff, erect.

*Opening.*—Petals fold outward with little curling.

Bloom:

*Size.*—Medium. Average open size is 3½ inches.

*Borne.*—Singly and in clusters, rounded.

*Stems.*—Short.

*Form.*—When first open, flat. Permanence: Retains its form to the end.

*Petalage.*—Number of petals under normal conditions: 20–25.

*Color.*—Center of flower: Upper side of petals Red 43A; reverse side of petals Red 42A; base of petals have large yellow area on upper side, very small yellow area on lower side. General tonality from a distance, Red 43A.

*Variegations.*—An occasional lighter streak.

*Discoloration.*—General tonality at end of first day: Near Red 43B. Third day: Near Red 43C.

*Fragrance.*—None.

Petals:

*Texture.*—Thick.

*Shape.*—Nearly round.

*Form.*—Tips slightly recurved.

*Arrangement.*—Imbricated. Petaloids in center, few.

*Persistence.*—Drop off cleanly.

*Lastingness.*—On the plant, long. As cut flower, long.

Reproductive parts:

*Anthers.*—Large. Color: Yellow. Arrangement: Regular around styles.

*Filaments.*—Color: Orange-Red 30A.

*Pollen.*—Gold yellow.

*Styles.*—Color: White lower half, reddish distal half.

*Stigmas.*—Color: Yellow.

PLANT

Form: Bush.
Growth: Very vigorous, upright.
Foliage: Number of leaflets on normal mid-stem leaves: 5 or 7.
*Size.*—Medium.
*Quantity.*—Abundant.
*Color.*—New foliage: Grayed Purple 183A. Old foliage: Green 147.
Leaflets:
*Shape.*—Oval.
*Texture.*—Upper side: Leathery, glossy.
*Edge.*—Serrated.
*Serration.*—Single, small.
*Petiole.*—Rachis: Color: Reddish. Underside: Prickles.
*Stipules.*—Long, bearded.
*Disease resistance.*—Very resistant to mildew, blackspot under normal growing conditions at Irvine, Calif.

Wood:
*New wood.*—Color: Reddish. Bark: Smooth.
*Old wood.*—Color: Green. Bark: Smooth.
Prickles:
*Quantity.*—On main stalks from base, many. On laterals from stalk, many.
*Form.*—Long, hooked downward.
*Color when young.*—Red.
*Position.*—Irregular.
Small prickles:
*Quantity.*—On main stalks, many. On laterals, many.
*Color.*—Brown.

I claim:

1. A new and distinct variety of rose plant of the floribunda class, substantially as herein shown and described, characterized particularly as to novelty by the unique combination of its floribunda habit plant, with mildew resistant foliage, bearing orange-red, non-fragrant blooms.

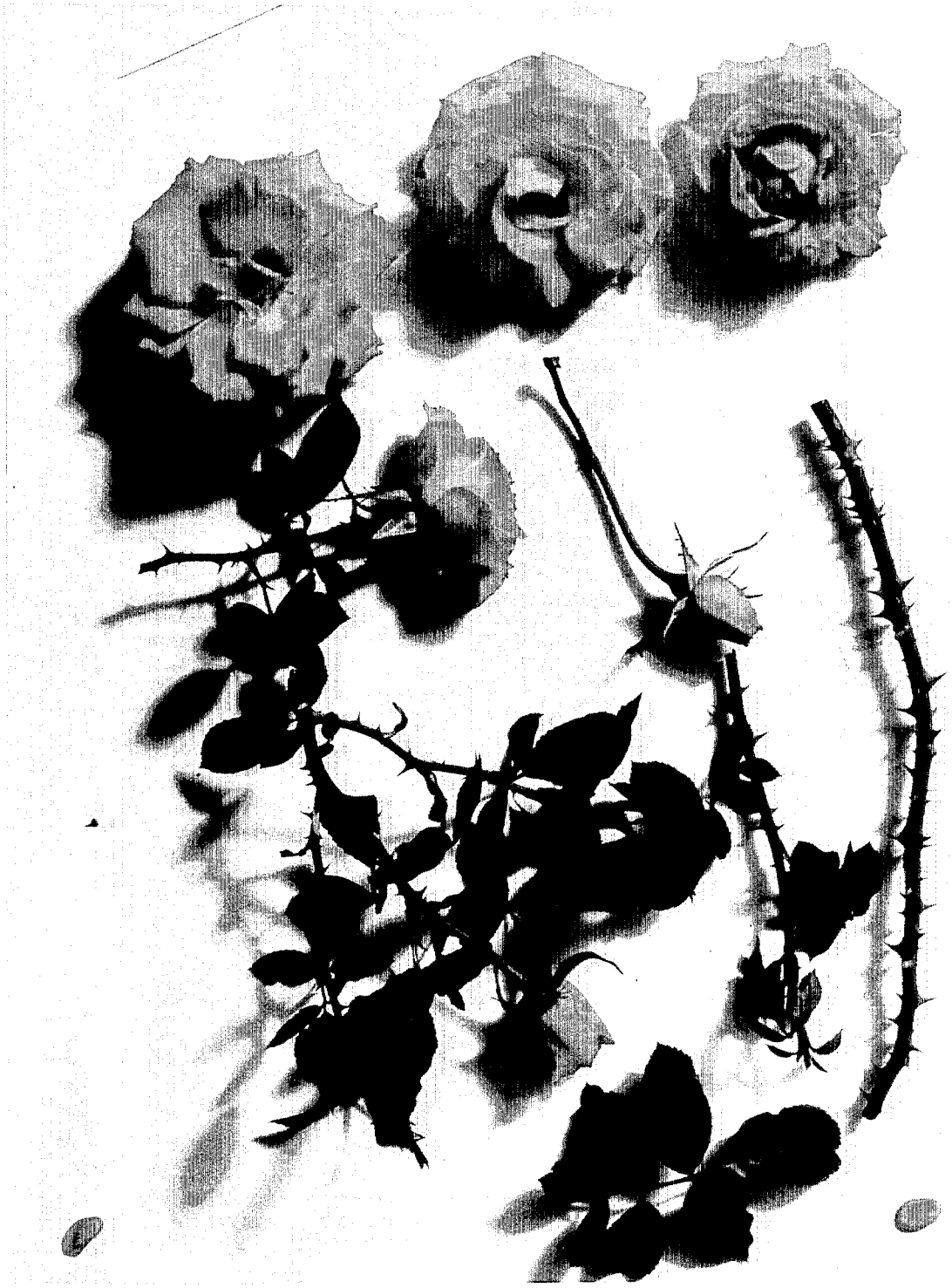

* * * * *